United States Patent [19]
Köckerling et al.

[11] Patent Number: 5,626,591
[45] Date of Patent: May 6, 1997

[54] SURGICAL ANASTOMOSIS RING INSERTION DEVICE

[76] Inventors: Ferdinand Köckerling, Hindenburgstrasse 28a, D-91054, Erlangen; Ignaz Schneider, Haupstrasse 52, D-91301, Forchheim, both of Germany

[21] Appl. No.: 392,110

[22] Filed: Feb. 22, 1995

[30] Foreign Application Priority Data

Mar. 9, 1994 [DE] Germany ............... 44 07 668.1

[51] Int. Cl.$^6$ ........................................ A61B 17/11
[52] U.S. Cl. ............................. 606/153; 606/151
[58] Field of Search ........................ 606/151, 150, 606/153–156, 104; 673/1, 12

[56] References Cited

U.S. PATENT DOCUMENTS

| | | | |
|---|---|---|---|
| 4,667,673 | 5/1987 | Li | 606/153 |
| 4,917,091 | 4/1990 | Berggren et al. | 606/153 |
| 5,464,415 | 11/1995 | Chen | 606/153 |
| 5,503,635 | 4/1996 | Saver et al. | 606/153 |

FOREIGN PATENT DOCUMENTS

| | | |
|---|---|---|
| 0564783 | 10/1993 | European Pat. Off. . |
| 0568774 | 11/1993 | European Pat. Off. . |
| 9200967 | 7/1992 | Germany . |

*Primary Examiner*—Jeffrey A. Schmidt
*Attorney, Agent, or Firm*—Laff, Whitesel, Conte & Saret, Ltd.

[57] ABSTRACT

A surgical anastomosis ring insertion device is provided with a leading-in tube insertable into the intestinal tract, with a cylindrical retaining head, disposed on the distal end of the leading-in tube, for the anastomosis ring, with a slider mechanism for engaging and locking the anastomosis ring, the slider mechanism being disposed in the vicinity of the retaining head and actuatable by way of a transmission from the proximal end of the leading-in tube, and with a drive, disposed on the proximal end of the leading-in tube, for the transmission of the slider mechanism.

9 Claims, 5 Drawing Sheets

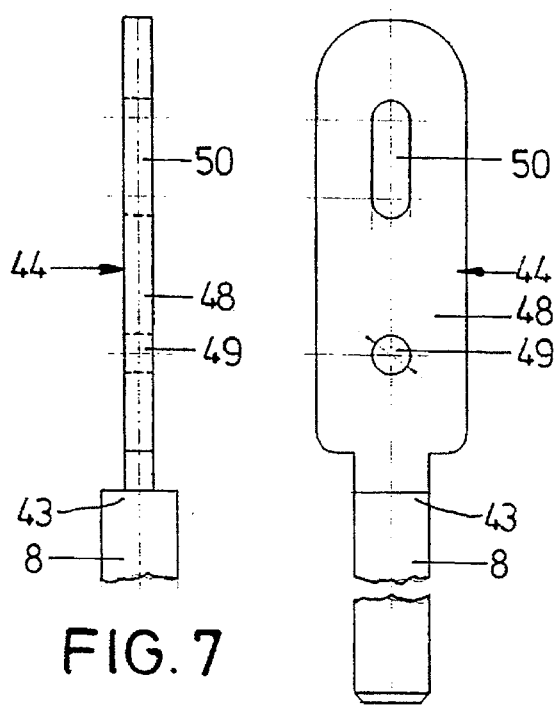
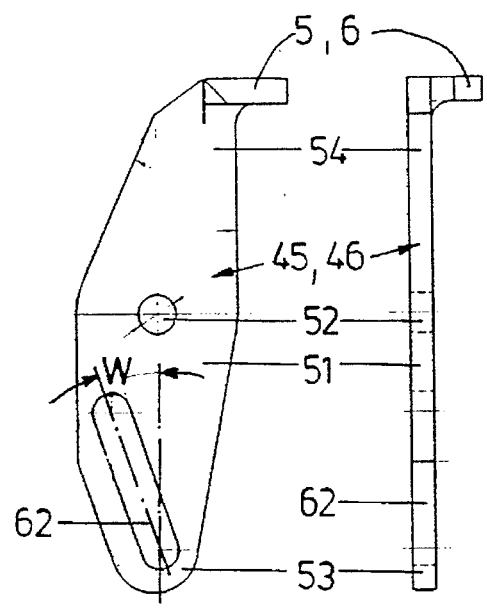
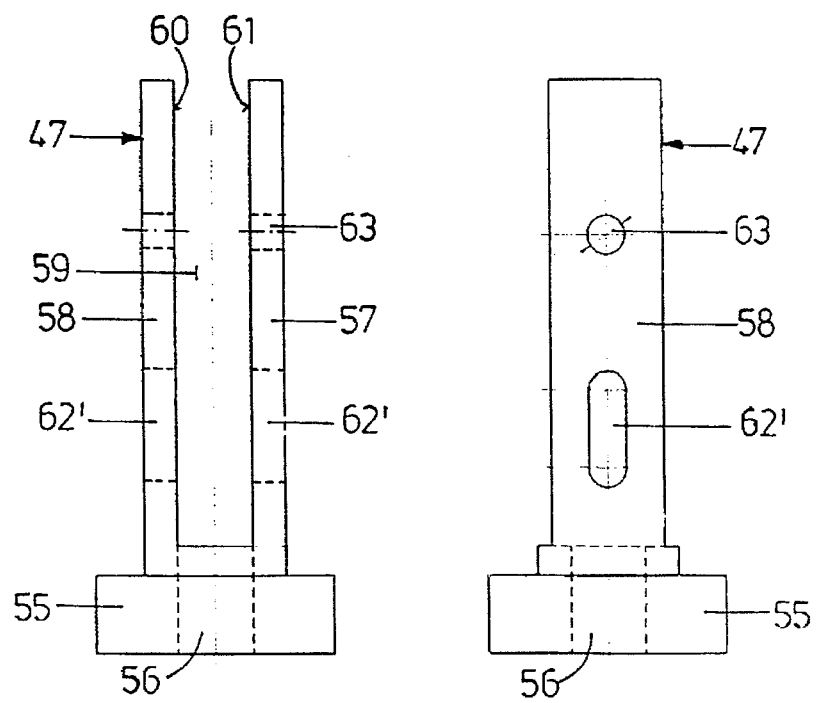

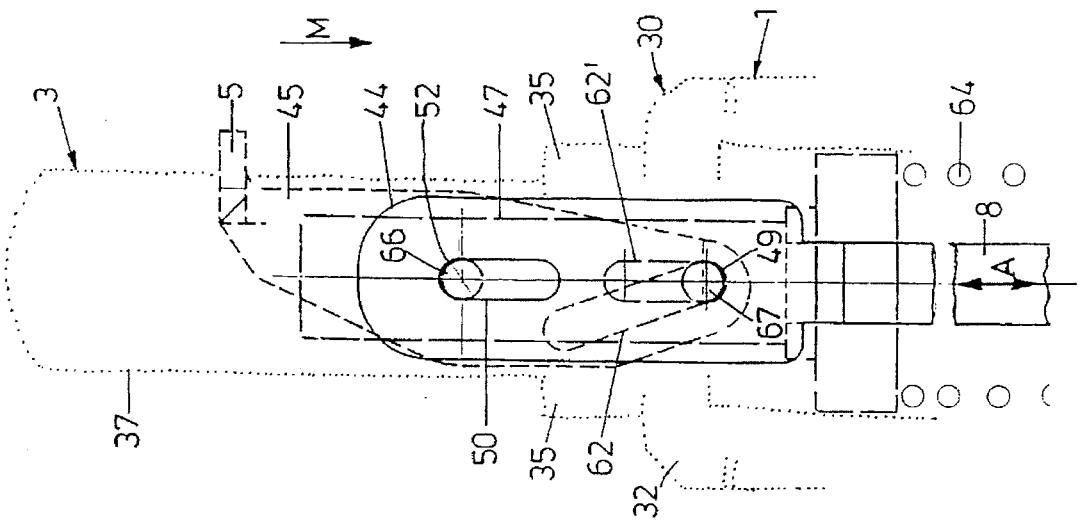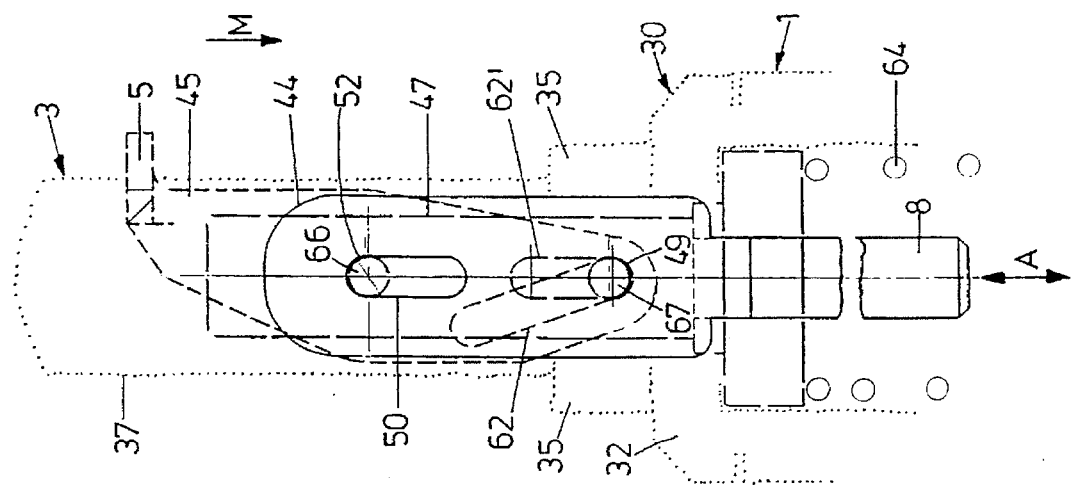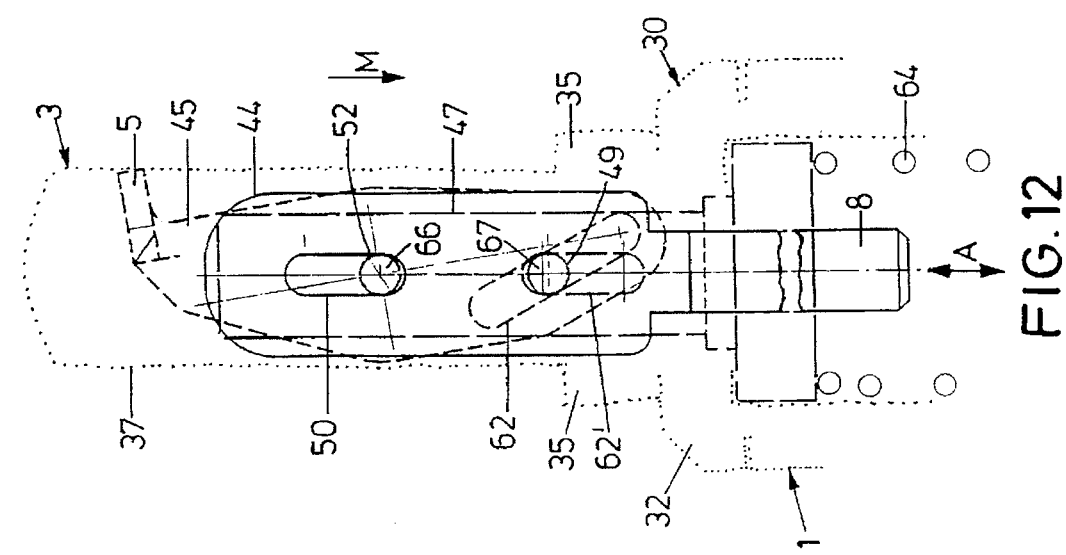

5,626,591

SURGICAL ANASTOMOSIS RING INSERTION DEVICE

BACKGROUND OF THE INVENTION

1. Field of the Invention

The invention relates to a surgical anastomosis ring insertion device to be used in invasive or laparoscopic intestinal surgery.

2. Background Art

The removal of for instance cancerous portions of the intestine poses the problem of joining the severed ends of the bowel. This problem is usually solved with the aid of so-called anastomosis rings commercially available for instance under the trademark "VALTRAC"®. Biofragmentable anastomosis rings of the generic type consist of two members of mushroom configuration, of which the shanks are guided to telescope one within the other, forming a passage for the intestinal contents. The approximately hemispherical heads of these members are arranged in opposite directions. Their peripheral edges facing each other can join the two severed ends of the intestinal lumen by the two members being pushed together and locked in their position of engagement. To this end, the two severed ends are each provided with a so-called purse string suture, the two heads of mushroom configuration of the anastomosis ring are inserted into the two open intestinal lumens, the severed ends are moved over the shanks of the ring and tightened with the aid of the purse string suture, and then the two members are pushed together and locked. This produces a tight connection of the two open intestinal lumens, the ring disintegrating and being discharged within a period of about two to three weeks as result of its biofragmentability.

This known method of inserting an anastomosis ring has the disadvantage that the ring members in their inserted position must be pushed together and locked from outside by access to the intestinal wall.

Consequently, this surgical technique cannot be used in laparoscopic surgery nor even in invasive surgery—with cramped conditions prevailing as for instance in the case of rectal surgery.

SUMMARY OF THE INVENTION

It is accordingly the object of the invention to embody a surgical anastomosis ring insertion device, with the aid of which the above-mentioned surgical technique becomes applicable even in laparoscopic surgery or under cramped conditions even in invasive surgery.

According to the invention, this object is attained by the anastomosis ring insertion device comprising a leading-in tube preferably rectally insertable into the intestinal tract, a cylindrical anastomosis ring retaining head disposed on the distal end of the leading-in tube, a slider mechanism, disposed in the vicinity of the retaining head, for engaging and locking the anastomosis ring, and a drive for the slider mechanism disposed on the proximal end of the leading-in tube. The slider mechanism is actuatable by way of a transmission from the proximal end of the leading-in tube.

The afore-mentioned design of the anastomosis ring insertion device dispenses with the necessity to effect the engagement and the locking of the ring by direct manipulation of the ring from the outside of the portions of the intestine to be joined. So the ring can be positioned at any hidden or badly accessible place.

Further features, details and advantageous embodiments of the anastomosis ring insertion device according to the invention will become apparent from the subclaims and the ensuing description of an examplary embodiment of the subject matter of the invention taken in conjunction with the attached drawing.

BRIEF DESCRIPTION OF THE DRAWING

FIGS. 6 and 7 are two different lateral views of the control slider, FIGS. 8 and 9 are two different lateral views of a driving lever, FIGS. 10 and 11 are two different lateral views of the bearing slider of the insertion device of FIG. 1, and FIGS. 12 to 14 are an operational chart of the driver actuation of the insertion device of FIG. 1.

DESCRIPTION OF THE PREFERRED EMBODIMENT

Figure 1:
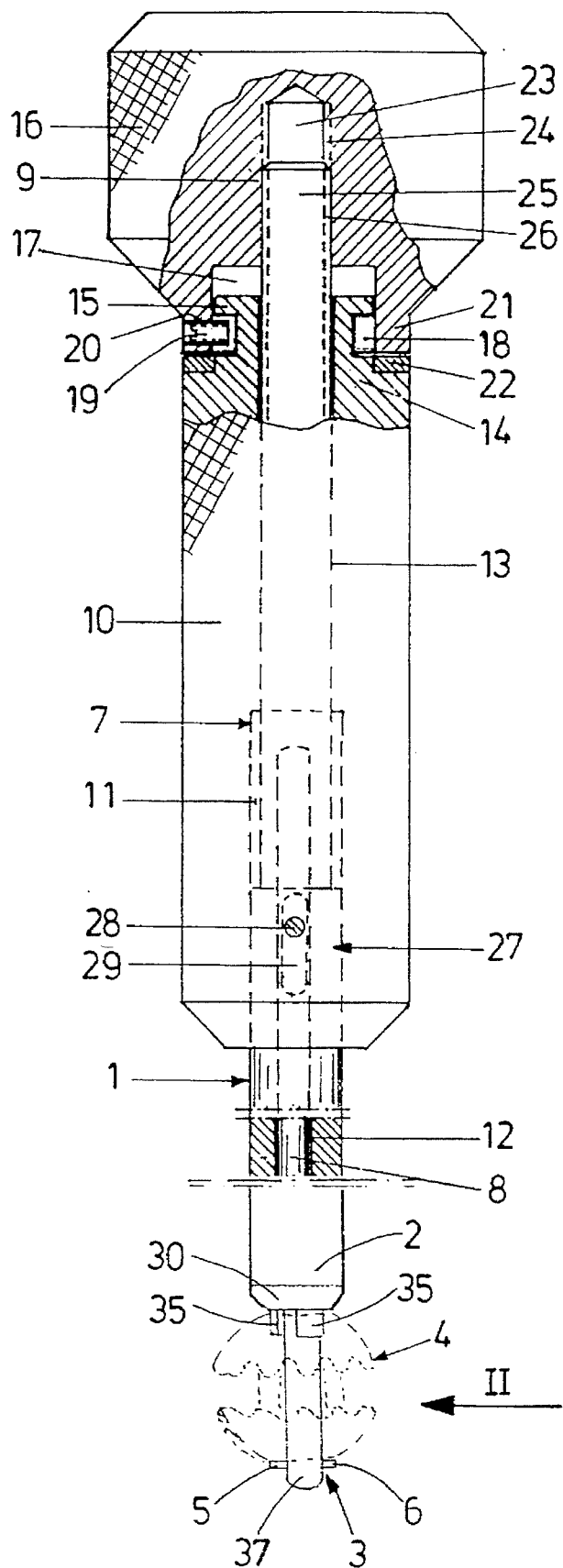
FIG. 1 is a lateral view of an anastomosis ting insertion device according to the invention in a partial sectional illustration, 2 is a lateral view of the head portion of the insertion device seen in the direction of arrow II of FIG. 1.

As seen from FIG. 1, an anastomosis ring insertion device according to the invention comprises a leading-in tube 1 as a substantial component, which is rectally insertable into the intestinal tract and may be straight or bent. A substantially cylindrical retaining head 3 for a conventional VALTRAC® anastomosis ring 4 is disposed on the distal end 2 of the leading-in tube 1. A slider mechanism still to be specified, of which the two lateral drivers 5, 6 are to be seen in FIG. 1, is disposed within the retaining head 3 and serves to push the anastomosis ring 4 together and to lock it. From the proximal end 7 of the leading-in tube 1, the slider mechanism is actuatable by way of a transmission provided with a drive disposed on the proximal end 7 of the leading-in tube 1.

The transmission and the drive for the slider mechanism are formed as follows by a push bar 8 extending in the leading-in tube 1 and comprising a spindle drive 9:

A substantially cylindrical handle member 10 is coaxially screwed on to the proximal end 7 of the leading-in tube 1 by means of the screw connection 11, the handle member 10 having a continuous inner bore 13 extending coaxially with the tube orifice 12. An annular shoulder 15 likewise extending coaxially, on which the cylindrical internal opening 17 of a spindle wheel 16 is rotatably supported, is provided at the front end 14, facing away from the leading-in tube 1, of the handle member 10. A circumferential groove 18, with which headless screws 19 engage as projections from the outside, is further provided on the circumference of the annular shoulder 15. These headless screws 19 are screwed through corresponding threaded bores 20 in the annular collar 21 around the cylindrical internal opening 17 of the spindle wheel 16, arresting the latter in the longitudinal axial direction of the leading-in tube 1. A sliding ring 22 of brass is inserted between the front side of the annular collar 21 and the handle member 10.

With its bottom hole 23 which comprises an internal thread 24 and which, proceeding from the internal opening 17, is disposed coaxially to the longitudinal axis A of the leading-in tube 1, the spindle wheel 16 cooperating with a threaded bolt 25 in the inner bore 13 of the handle member 10 forms a spindle drive 9 for the slider mechanism. To this end, the external thread 26 of the threaded bolt 25 is in engagement with the internal thread 24 in the spindle wheel 16. Furthermore, at its end 27 facing away from the spindle wheel 16, the threaded bolt 25 is connected with the push bar 8, which leads to the slider mechanism on the distal end 2 of the leading-in tube 1. As a result of the construction specified above, the threaded bolt 25 cooperating with the push bar 8 forms a transmission for transmitting the rotary actuation originating from the spindle wheel 16 to the slider mechanism. In this case, the unit of the threaded bolt 25 and the push bar 8 is further arrested in the direction of rotation. For the purpose of this arrest of rotation, the threaded bolt 25 is provided on its outside with a radially projecting elevation in the form of a screw head 28 of a screw radially screwed into the threaded bolt, which screw head 28 engages with an oblong hole 29 extending parallel to the longitudinal axis A of the leading-in tube 1 in the latter.

Figure 2:
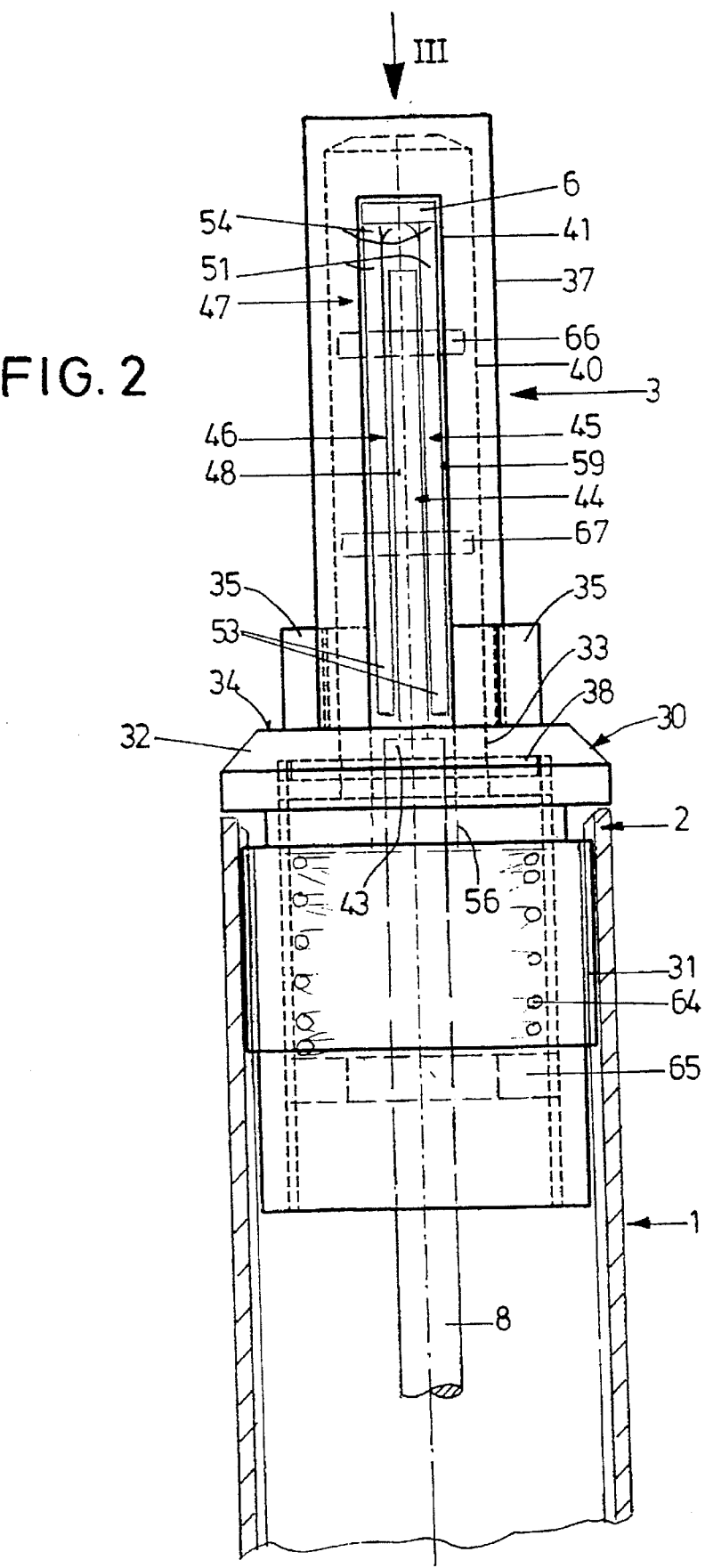
Figure 5:
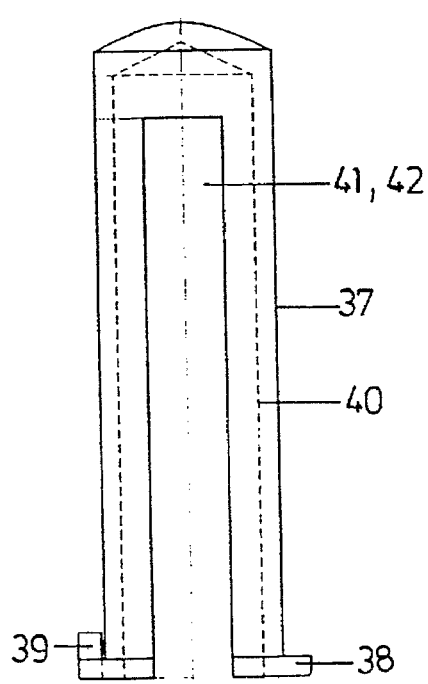
FIG. 5 is a lateral view of the head casing of the insertion device.
Figure 4:
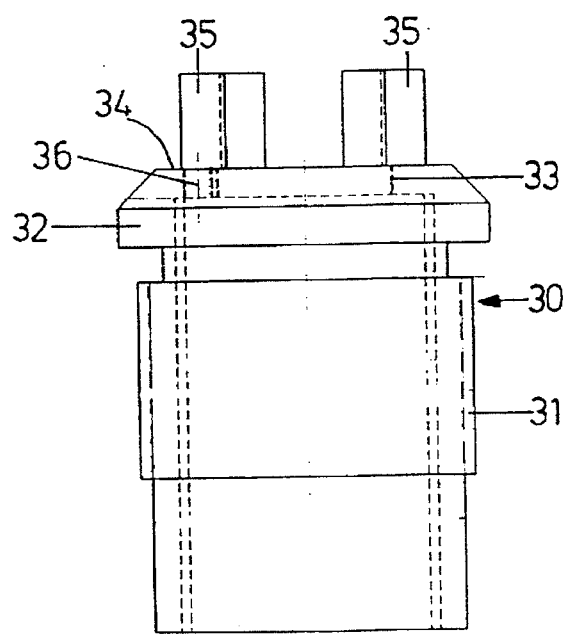
FIG. 4 is a lateral view of the head base of the insertion device.

The fundamental structure of the retaining head 3 will be explained taken in conjunction with FIG. 2. On the one hand, this retaining head 3 comprises a substantially cylindrical head base 30, of which the cylindrical hollow threaded portion 31 is screwed into the internal opening at the distal end 2 of the leading-in tube 1. An annular collar 32 closely bears against the front edge of the leading-in tube 1. The head base 30 is further provided with a coaxial throughhole 33, which, on the front end 34 of the collar 32, is surrounded by two diametrically disposed centering shoulders 35 for the anastomosis ring 4. A small, axial-parallel bore 36 is located on the bottom of the threaded portion 31 by the side of the throughhole 33 (FIG. 4). This bore 36 serves for the arrest of rotation of the head casing 37 (FIG. 5), which is pushed through the throughhole 33 from the side of the threaded portion 31 until the lower end of its collar 38 abuts on the inside of the collar 32 of the head base 30. A pin 39 on the upper side of the collar 38 engages with the bore 36 for the mentioned arrest of rotation.

The head casing 37 is in the form of a cap, having an axial-parallel, cylindrical bearing bore 40 as well as wall openings 41, 42 likewise axial-parallel, which face each other radially and are oblong rectangular in lateral view (FIG. 5), for the accommodation of the slider mechanism still to be explained. The wall openings 41, 42 are open in the vicinity of the collar 38.

The slider mechanism comprises a control slider 44 (FIGS. 6, 7) shaped in one piece with the distal end 43 of the push bar 8, two driving levers 45, 46 (FIGS. 8, 9) as well as a bearing slider 47 (FIGS. 10, 11).

The control slider 44 is a plain, substantially rectangular plate member 48 having a bearing bore 49 and an axial-parallel oblong hole 50 situated one behind the other in the axial-parallel direction. The two double-armed driving levers 45, 46 consist of an approximately rhombic plate member 51 provided with a pivot bearing bore 52 disposed centrally and, in the vicinity of the rear end 53, with an oblong hole 62 extending at an acute angle W relative to the longitudinal axis A. The driver 5, 6 is molded on the second end 54 of the plate member 51, laterally projecting at right angles from the latter (FIGS. 8, 9).

The bearing slider 47 (FIGS. 10, 11) consists of a cylindrical base 55 which is provided with a rotationally symmetrical throughhole 56 opening between the two axial-parallel fork legs 57, 58 of the bearing slider 47. The two fork legs 57, 58 cooperate to have a cylindrical contour and to form a gap 59 between them, which is defined by the plain inside walls 60, 61 of the fork legs 57, 58. In these fork legs 57, 58 further provision is made for an axial-parallel oblong hole 62' facing the base 55 as well as for another pivot bearing bore 63 approximately centrally between the oblong hole 62' and the free end of the fork legs 57, 58.

Figure 3:
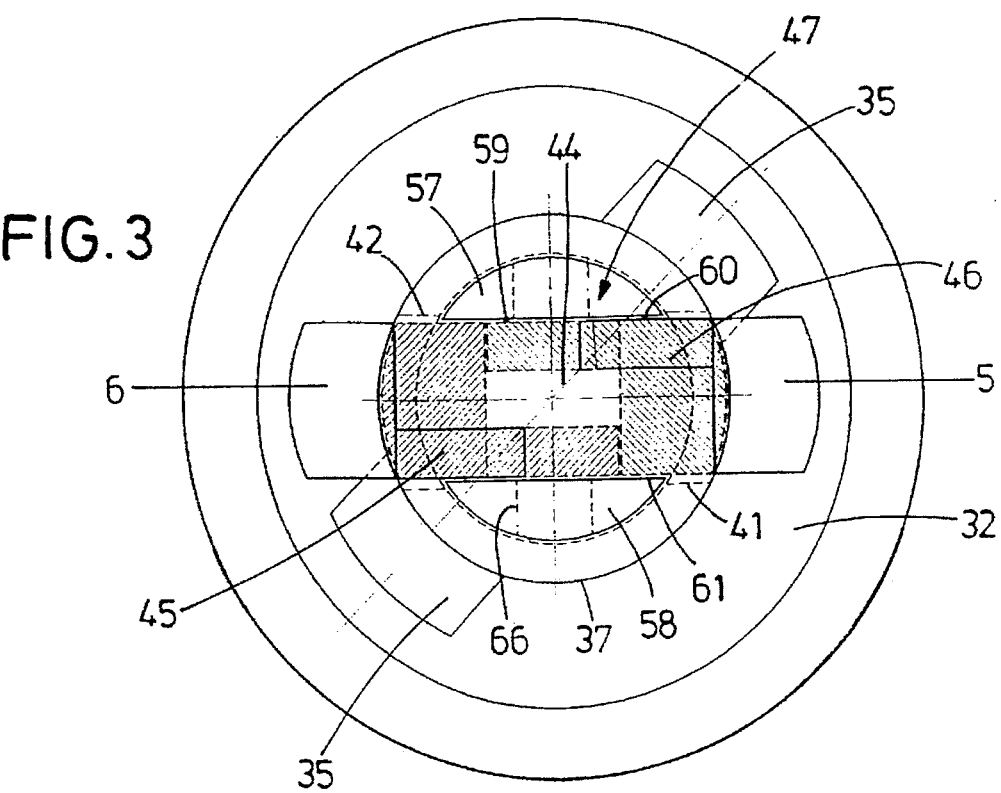
FIG. 3 is a plan view of the insertion device seen in the direction of arrow III of FIG. 2.

The control slider 44, the driving levers 45, 46 and the bearing slider 47 are disposed in the retaining head in the following way (FIGS. 2, 3):

From the side of the leading-in tube 1, the bearing slider 47 is pushed into the bearing bore 40 of the head casing 37 until its base 55 rests on the collar 38 of the head casing 37. A helical compression spring 64 is disposed before the base 55 and bears against a thrust bearing 65 screwed into the threaded portion 31 of the head base 30. Thus, the bearing slider 47 is spring-biased counter to the direction of driving M in relation to the anastomosis ring 4.

The fork legs 57, 58 of the bearing slider 47 are located within the bearing bore 40 of the head casing 37 and are oriented such that the receiver gap 59 is flush with the wall openings 41, 42 of the head casing 37. The push rod 8 extends through the throughhole 56 of the bearing slider 47 in such a way that the control slider 44 integrally molded thereon rests centrally between the two fork legs 57, 58. On either side of the control slider 44, one of the two driving levers 45, 46 is placed into the receiver gap 59, the main planes of the control slider 44 and of the driving levers 45, 46 extending parallel to each other and parallel to the inside walls 60, 61 of the fork legs 57, 58.

The two driving levers 45, 46 are pivotably supported on the bearing slider 47 by way of a pivot bolt 66, which passes through each of their pivot bearing bores 52 and of which the ends reside in the opposite pivot bearing bores 63 of the bearing slider 47. This pivot bolt 66 reaches through the oblong hole 50 in the control slider 44.

In the bearing bore 49 of the control slide 44, a control bolt 67 is inserted, projecting on either side and extending in the oblong holes 62, 62' provided in the driving levers 45, 46 and in the bearing slider 47. The oblong holes 50, 62 and 62' of the control slider 44, of the driving levers 45, 46 and of the bearing slider 47, respectively, serve as driving links for the controlled pivoting and displacing of the driving levers 45, 46.

The functioning of the insertion device according to the invention is to be explained as follows, taken in conjunction with FIGS. 12 to 14, attention being drawn to the fact that only one driving lever 45 is shown in these drawings for reasons of clearness. The second driving lever 46 is mirror symmetrical to the first driving lever 45 referred to the longitudinal axis A and it performs the same movements synchronously and diametrically opposed referred to the radial pivoting of the drivers.

FIG. 12 illustrates the receiving position of the insertion device, in which the driving lever 45 (outlined by a line of short dashes) is pivoted radially inwards so that the driver 5 lies within the contour (outlined by a dotted line) of the head casing 37. In this position, the internal opening of an anastomosis ring 4 can be pushed on the shank formed by the head casing 37, where the anastomosis ring 4 is centered and arrested in the direction of rotation with the aid of the centering shoulders 35. Then the spindle wheel 16 is actuated so that the push bar 8 is moved in the direction toward the proximal end 7 and, consequently, the control slider 44 (shown in solid lines) in the direction of driving M. As a result of the linked control of the control bolt 67 and the inclined oblong hole 62 in the driving lever 45, the latter is pivoted clockwise referred to FIG. 12 about the pivot bolt 66. The pivot bolt 66 forms a fixed center of motion for the driving lever 45, the spring-biased bearing slider 47 (outlined by a line of long dahes) retaining it in the position shown in FIG. 12. As a result of the relative displacement of the control slider 44 relative to the bearing slider 47 and the driving lever 45, the pivot bolt 66 passes through the oblong hole 50 in the control lever 44.

FIG. 13 illustrates the swung-out position of the driving lever 45, in which the driver 5 projects from the contour of the casing 37, backing up the anastomosis ring 4. In this position, the control bolt 67 rests on the lower end of the oblong hole 62' of the bearing slider 47 as well as on the lower end of the inclined oblong hole 62 in the driving lever 45. Further, the pivot bolt 66 has moved within the oblong hole 50 of the control slider 44 to the upper end of the oblong hole 50. In the case of further displacement of the push bar 8 in the direction towards the proximal end 7, the control bolt 67 of the control slider 44 drives the bearing slider 47 in this direction counter to the action by the helical compression spring 64. In a synchronous motion the pivot bolt 66 is driven in the same direction by the upper end of the oblong hole 50 in the control slider 44, so that the control slider 44, the bearing slider 47 and in particular the driving lever 45 are displaced in the direction towards the proximal end 7. As a result, the driver 5 acts upon the anastomosis ring 4, pushing the latter's two members together until the two members of the anastomosis ring are in locking engagement and the connection between the two intestinal portions has been produced (FIG. 14).

In the case of reverse actuation of the spindle wheel 16, the push bar 8 and the control slider 44 are displaced in the opposite direction, the bearing slider 47 and, consequently, the driving lever 45 being moved again into the position of FIG. 13 by the action of the helical compression spring 64. In the case of further displacement of the push bar 8 and the control slider 44, the driving lever 45 is again pivoted radially inwards until the position of FIG. 12 has been taken. In this position, the retaining head 3 can be released from the anastomosis ring 4 placed in the bowel and the inserting device can be removed from the intestinal tract.

What is claimed is:

1. A surgical anastomosis ring insertion device comprising:
   a leading-in tube (1) insertable into an intestinal tract of a patient and having a distal end (2) and a proximal end (7),
   a cylindrical anastomosis ring (4) retaining head (3) disposed on the distal end (2) of the leading-in tube (1),
   a slider mechanism, disposed in the vicinity of the retaining head (3), for engaging and locking the anastomosis ring (4),
   a transmission (9) for actuating said slider mechanism from the proximal end (7) of the leading-in tube (1), and
   a drive (16), disposed on the proximal end (7) of the leading-in tube (1), for the transmission (9) of the slider mechanism, wherein the drive and the transmission for the slider mechanism are designed as a spindle drive (9), which comprises a spindle wheel (16) arrested longitudinally axially in relation to a longitudinal axis (A) of the leading-in tube (1) and rotatably supported coaxially thereto and a push bar (8), which is arrested in a direction of rotation and displaceable longitudinally axially in the leading-in tube (1) and of which an external thread (26), on an outer end (27) of the push bar (8), is in engagement with an internal thread (24) of the spindle wheel (16) and a distal end (43) of which push bar (8) is coupled with the slider mechanism.

2. An insertion device according to claim 1, wherein the slider mechanism has at least one driver (5,6), which is displaceable in two operational steps, i.e. on the one hand it is radially displaceable from a position retracted into the retaining head (3) into a position laterally projecting from the retaining head (3), and on the other hand, in its projecting position, while driving the anastomosis ring (4), it is axially displaceable into the position of locking of the anastomosis ring (4).

3. An insertion device according to claim 2, wherein in each case one driver (5, 6) is disposed on one of two driving levers (45, 46), which are pivotable out of the retaining head (3) radially in opposite direction and longitudinally axially displaceable and which are pivotably positioned in a bearing slider (47), the driving levers (45, 46) and the bearing slider (47) being coupled, by way of a driving link arrangement (50, 62, 62'), with a control slider (44) connected with the transmission (9).

4. A insertion device according to claim 3, wherein the control slider (44) is integrally formed on a distal end (43) of the push bar (8) of the transmission (9).

5. A surgical anastomosis ring insertion device comprising:
   a leading-in tube (1) insertable into an intestinal tract of a patient and having a distal end (2) and a proximal end (7),
   a cylindrical anastomosis ring (4) retaining head (3) disposed on the distal end (2) of the leading-in tube (1),
   a slider mechanism, disposed in the vicinity of the retaining head (3), for engaging and locking the anastomosis ring (4),
   a transmission (9) for actuating said slider mechanism from the proximal end (7) of the leading-in tube (1), and
   a drive (16), disposed on the proximal end (7) of the leading-in tube (1), for the transmission (9) of the slider mechanism, wherein the slider mechanism has at least one driver (5,6), which is displaceable in two operational steps, i.e. on the one hand it is radially displaceable from a position retracted into the retaining head (3) into a position laterally projecting from the retaining head (3), and on the other hand, in its projecting position, while driving the anastomosis ring (4), it is axially displaceable into the position of locking of the anastomosis ring (4), wherein in each case one driver (5,6) is disposed on one of two driving levers (45, 46), which are pivotable out of the retaining head (3) radially in opposite direction and longitudinally axially displaceable and which are pivotably positioned in a bearing slider (47), the driving levers (45, 46) and the bearing slider (47) being coupled, by way of a driving link arrangement (50, 62, 62'), with a control slider (44) connected with the transmission (9), and wherein the bearing slider (47) axially displaceable in relation to the retaining head (3) and to the control slider (44) is spring biased counter to a driving direction (M) of the driver (5, 6).

6. An insertion device according to claim 5, wherein the driving link arrangement comprises, on the one hand, a first elongated driving link (62) provided in each driving lever (45, 46) and extending at an acute angle (W) relative to the longitudinal axis (A) of the leading-in tube (1), and on the other hand, a second elongated driving link (62') provided in the bearing slider (47) and extending axial-parallel, a control bolt (67) disposed in the control slider (44) engaging with the driving links (62, 62').

7. A surgical anastomosis ring insertion device comprising:

a leading-in tube (1) insertable into an intestinal tract of a patient and having a distal end (2) and a proximal end (7), a cylindrical anastomosis ring (4) retaining head (3) disposed on the distal end (2) of the leading-in tube (1), a slider mechanism, disposed in the vicinity of the retaining head (3), for engaging and locking the anastomosis ring (4), a transmission (9) for actuating said slider mechanism from the proximal end (7) of the leading-in tube (1), and a drive (16), disposed on the proximal end (7) of the leading-in tube (1), for the transmission (9) of the slider mechanism, wherein the slider mechanism has at least one driver (5,6), which is displaceable in two operational steps, i.e. on the one hand it is radially displaceable from a position retracted into the retaining head (3) into a position laterally projecting from the retaining head (3), and on the other hand, in its projecting position, while driving the anastomosis ring (4), it is axially displaceable into the position of locking of the anastomosis ring (4), wherein in each case one driver (5,6) is disposed on one of two driving levers (45, 46), which are pivotable out of the retaining head (3) radially in opposite direction and longitudinally axially displaceable and which are pivotably positioned in a bearing slider (47), the driving levers (45, 46) and the bearing slider (47) being coupled, by way of a driving link arrangement (50, 62, 62'), with a control slider (44) connected with the transmission (9), and wherein the driving link arrangement comprises a third elongated driving link (50) of axial-parallel extension, which is provided in a control slider (44) and through which a pivot bolt (66) passes for pivotably supporting the driving levers (45, 46) on the bearing slider (47).

8. A surgical anastomosis ring insertion device comprising:

a leading-in tube (1) insertable into an intestinal tract of a patient and having a distal end (2) and a proximal end (7), a cylindrical anastomosis ring (4) retaining head (3) disposed on the distal end (2) of the leading-in tube (1), a slider mechanism, disposed in the vicinity of the retaining head (3), for engaging and locking the anastomosis ring (4), a transmission (9) for actuating said slider mechanism from the proximal end (7) of the leading-in tube (1), and a drive (16), disposed on the proximal end (7) of the leading-in tube (1), for the transmission (9) of the slider mechanism, wherein the slider mechanism has at least one driver (5,6), which is displaceable in two operational steps, i.e. on the one hand it is radially displaceable from a position retracted into the retaining head (3) into a position laterally projecting from the retaining head (3), and on the other hand, in its projecting position, while driving the anastomosis ring (4), it is axially displaceable into the position of locking of the anastomosis ring (4), wherein in each case one driver (5,6) is disposed on one of two driving levers (45, 46), which are pivotable out of the retaining head (3) radially in opposite direction and longitudinally axially displaceable and which are pivotably positioned in a bearing slider (47), the driving levers (45, 46) and the bearing slider (47) being coupled, by way of a driving link arrangement (50, 62, 62'), with a control slider (44) connected with the transmission (9), and wherein the bearing slider (47) is forked, the control slider (44) and the driving levers (45, 46) being disposed between two fork legs (57, 58) of the bearing slider (47).

9. A surgical anastomosis ring insertion device comprising:

a leading-in tube (1) insertable into an intestinal tract of a patient and having a distal end (2) and a proximal end (7), a cylindrical anastomosis ring (4) retaining head (3) disposed on the distal end (2) of the leading-in tube (1), a slider mechanism, disposed in the vicinity of the retaining head (3), for engaging and locking the anastomosis ring (4), a transmission (9) for actuating said slider mechanism from the proximal end (7) of the leading-in tube (1), and a drive (16), disposed on the proximal end (7) of the leading-in tube (1), for the transmission (9) of the slider mechanism, wherein the slider mechanism has at least one driver (5,6), which is displaceable in two operational steps, i.e. on the one hand it is radially displaceable from a position retracted into the retaining head (3) into a position laterally projecting from the retaining head (3), and on the other hand, in its projecting position, while driving the anastomosis ring (4), it is axially displaceable into the position of locking of the anastomosis ring (4), wherein in each case one driver (5,6) is disposed on one of two driving levers (45, 46), which are pivotable out of the retaining head (3) radially in opposite direction and longitudinally axially displaceable and which are pivotably positioned in a bearing slider (47), the driving levers (45, 46) and the bearing slider (47) being coupled, by way of a driving link arrangement (50, 62, 62'), with a control slider (44) connected with the transmission (9), and wherein the retaining head (3) has a cap-shaped head casing (37), which comprises an axial-parallel, cylindrical bearing bore (40) having axial-parallel, radially opposed wall openings (41, 42) for receiving the control slider (44), the bearing slider (47) and the driving levers (45, 46).

* * * * *